United States Patent [19]

Ninnis

[11] Patent Number: 5,426,362
[45] Date of Patent: Jun. 20, 1995

[54] DAMAGE DETECTION APPARATUS AND METHOD FOR A CONVEYOR BELT HAVING MAGNETICALLY PERMEABLE MEMBERS

[76] Inventor: Ronald M. Ninnis, 2525 York Ave, Vancouver, B.C., Canada, V6K 1E4

[21] Appl. No.: 954,680

[22] Filed: Sep. 30, 1992

[51] Int. Cl.6 .................. G01N 27/82; G01R 33/12
[52] U.S. Cl. ................... 324/235; 324/242; 340/676
[58] Field of Search ............... 324/235, 252, 251, 239, 324/240, 242, 243; 338/32 R, 32 H; 340/675, 676

[56] References Cited

U.S. PATENT DOCUMENTS

| | | | |
|---|---|---|---|
| 3,694,740 | 9/1972 | Bergstrand | 324/235 |
| 3,834,524 | 9/1974 | Ratz et al. | 340/676 |
| 4,087,800 | 5/1978 | Lee | 340/676 |
| 4,427,940 | 1/1984 | Hirama et al. | 324/240 |
| 4,660,018 | 4/1987 | Hatch | 338/32 R |
| 4,742,298 | 5/1988 | Ando et al. | 324/220 |
| 4,914,376 | 4/1990 | Meyer | 338/32 R |
| 5,146,163 | 9/1992 | Nawa | 340/676 |

FOREIGN PATENT DOCUMENTS 54-1333367 10/1979 Japan.
2012966 10/1977 United Kingdom.

OTHER PUBLICATIONS

Yasutaka Maekawa, Japanese Patent 57-204450, Detecting Method for Rock Mixed in Coal, Dec. 1982.

*Primary Examiner*—Sandra L. O'Shea
*Assistant Examiner*—Jay M. Patidar
*Attorney, Agent, or Firm*—Robert B. Hughes; Hughes, Multer & Schacht

[57] ABSTRACT

An apparatus to detect damage in the metallic magnetically permeable reinforcing cables in a conveyor belt. The apparatus includes a field coil to generate a magnetic field passing through the cables, and Hall effect sensors to detect change in reluctance in the field adjacent to the conveyor belt. The conveyor belt is moved relative to the apparatus so that when there is a damaged area, this will change the reluctance path, which changes the field intensity and is in turn detected by the Hall effect sensors.

6 Claims, 1 Drawing Sheet

DAMAGE DETECTION APPARATUS AND METHOD FOR A CONVEYOR BELT HAVING MAGNETICALLY PERMEABLE MEMBERS

BACKGROUND OF THE INVENTION

1. Field of the Invention

The present invention relates to electromagnetic sensing of damage and/or deterioration of objects made of, or incorporating, a magnetically permeable material, such as an elongate conveyor belt where reinforcing cables made of the magnetically permeable material are imbedded in (and thus largely concealed in) a relatively nonpermeable material such as a rubber-like structure of the belt.

2. Background Art

Large conveyor belts are used in a variety of applications, one of the major applications being in the mining industry where metal ore or other material is carried from the mine to a collecting location. For example, in an open pit mine, it is not uncommon to have a conveyor belt extending from a lower location upwardly for a distance as long as several thousand feet or even several miles. Such belts can possibly be as large as eight feet wide, and possibly as thick as four inches. The main belt material generally is a moderately flexible rubber-like material, and the belt is reinforced by a plurality of longitudinally extending metal cables which are positioned within the belt and extend along the length thereof.

One of the problems is that after continued use the metal reinforcing cables will deteriorate. For example, there may be a break in the conveyor belt material that would permit water or possibly even an acid (e.g. resulting from water reacting with the conveyed material) to come in contact with one or more of the cables to corrode the cables. The damage to the cables could come from an impact of some sort, or the deterioration could occur from natural wear or possibly fatigue of the metal because of long continued use. Sometimes the damage to the cable is a total break, and in some instances a partial deterioration that simply weakens the belt.

Since the metal cables in the belt are not visible, it is difficult to detect much of the damage to the cables. Unfortunately, when the damage is sufficiently severe so that it becomes outwardly visible, there may already have been a condition which would make further use of the belt dangerous. For this reason, it has usually been a practice in the industry to in a sense "overdesign" the belts so that there would be an adequately large margin of error to enable the belt to still function reasonably safely, even though there had been substantial degradation of the reinforcing cables.

Accordingly, an improved means of sensing deterioration (even a relatively small amount of deterioration) at an earlier time when it would not be visible by inspecting the outside of the belt would be advantageous.

SUMMARY OF THE INVENTION

The apparatus of the present invention is designed to detect anomalies in a magnetically permeable member. This apparatus comprises a field coil means adapted to produce a magnetic field in an operating area adjacent to the field coil means. It also comprises sensing means responsive to strength of the magnetic field at the operating area.

The apparatus is arranged to be positioned adjacent to the magnetically permeable member so that the member is located at the operating area of the apparatus. This is done in a manner so that there can be relative movement between the magnetically permeable material and the apparatus, so that, relative to the apparatus, the magnetically permeable material is passing through the operating area of the apparatus.

Variations in the permeability of the magnetically permeable member are sensed by the sensing means responding to variations in the magnetic field at the sensing means, with said variations in the magnetic field at the sensing means indicating an anomaly in a portion of the magnetically permeable member positioned at the operating area.

In a preferred form, the coil means is arranged both above and below the operating area so as to produce upper and lower flux fields. The sensing means further comprises an upper sensing means portion positioned above said operating area and a lower sensing means portion positioned below said operating area.

Also, there is alternating current supply means to supply alternating current to the coil means, so that alternating magnetic fields are produced at said operating area.

The apparatus is particularly adapted to detect anomalies in an elongate member having elongate magnetically permeable cord means extending lengthwise in said member. Further, the sensing means comprises a first set of sensing devices extending transversely over an upper surface of said member, and a second set of sensing devices extending transversely below a lower surface of said member.

In the preferred form, the sensing devices comprise Hall effect sensors.

In the method of the present invention, the member is moved through the operting area, and the sensing means is utilized to detect changes in the magnetic field intensity.

DESCRIPTION OF THE PREFERRED EMBODIMENT

Figure 1:
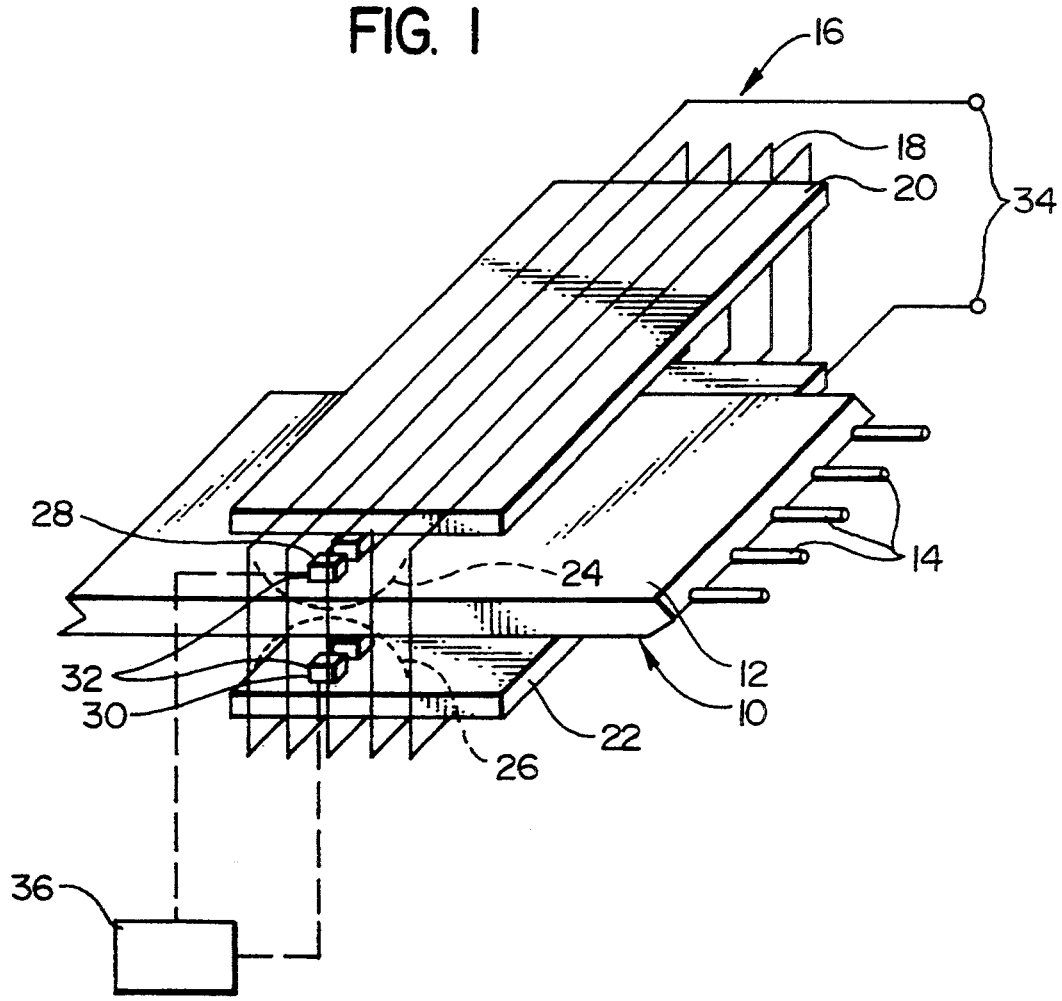
FIG. 1 is an isometric view of a preferred embodiment of the present invention.

With reference to FIG. 1, there is shown a portion of a conveyor belt 10 having a main body portion 12 made of a rubber-like moderately resilient material that has relatively low magnetic permeability. Embedded in the interior of the main body portion 12 is a plurality of elongate longitudinally extending cables 14 which are spaced laterally from one another along substantially the entire width of the belt. Typically, in a belt having a width of between 12 to 96 inches and a vertical thickness dimension of between about ½ to 4 inches, there could be as many as 20 to 240 cables, spaced from one another at intervals from about 0.45 to 1.0 inch (measured center line to center line). The diameter of such cables could be, in a typical belt, from as large as ½ inch.

The apparatus 16 of the present invention comprises a field coil 18 which extends in rectangular loops entirely around the conveyor belt 10. The upper and lower portions of the field coil 18 are located by upper and lower nonmagnetic formers 20 and 22, in the form of rectangular plates.

The field coil 18 creates upper and lower magnetic fields 24 and 26 which reach toward one another into an operating area within the field coil 18, with this operating area being the area through which the conveyor belt 16 or other member comprising magnetically permeable material passes. There are upper and lower sets, 28 and 30, respectively, of individual Hall effect sensors 32. The Hall effect sensors 32 of each set 28 and 30 extend in a transverse row from one side of the belt 10 to the other.

The field coil 18 is energized by a source of alternating current, indicated at 34. This alternating current would normally be within the audio range, and desirably at a frequency range of 100 to 1,000 Hz.

To describe the operation of the present invention, it will be noted that the magnetic field lines 24 and 26 lie parallel to the magnetically permeable cords 14 and will flow therethrough (due to the magnetic field lines encountering a path of lesser reluctance). The Hall effect sensors 32 above and below the belt 10 are placed within the magnetic field lines 24 and 26 and are positioned such that their active (that is magnetic flux sensing) axes will intersect the lines of flux 24 or 26. The output of each Hall effect sensor 32 will be a function of the ampere turn product of the field coil 18, the sensitivity to magnetic flux of the sensors 32 themselves, the position of each sensor 32 in relation to the magnetic field lines 24 or 26, the permeability of the cords or cables 14, and the position of the cords 14 in relation to the magnetic field lines 24 and 26.

However, it must be realized that the output of each Hall effect sensor 32 bears an inverse relationship to the two latter variables (i.e. the permeability of the reinforcing members 14, and the position of the members 14 in relation to the magnetic field lines 24 and 26) inasmuch as the magnitude of the output of the sensors 32 is a direct function of the strength of any intersecting magnetic flux. Therefore, the absence of any permeable material within the magnetic field generated by the coil 18 will appear as a strong flux (maximum field lines intersection) and thereby produce the highest output from the Hall effect sensors 32. The presence of any permeable material in the operating area will produce a path of lesser reluctance for the magnetic lines to follow and will thereby reduce the magnitude of the flux encountered by the Hall effect sensors 32, and correspondingly reduce the magnitude of their outputs.

One of the reasons that there are sensors 32 both above and below the belt 10 is that the belt 10 in traveling through the operating area has a tendency to "flutter" (i.e. vibrate up and down). In order to compensate for this flutter, the sensors 32 above and below the belt 10 can have their outputs summed together (in phase) in order to cancel vibrationally induced offsets in the magnetically permeable members 14.

One reason for using the alternating current to drive the field coil 18 is that the strength of the magnetic field generated by the coil 18 is insufficient to effect degaussing of the magnetically permeable members (i.e. remove any residual permanent magnetic fields therefrom). Rather, the alternating magnetic field approach is utilized in order to perform "synchronous detection or sampling", which does allow removal of the effects of permanent magnetization and other static offsets (such as positional displacement or misalignment of the belt in the vertical axis).

Alternatively, instead of using the Hall effect sensors, it would be possible to use magneto resistive probes. The latter are more sensitive, but requires a biasing field and may need to be periodically reset.

As another possibility, the distance from the sensor to the belt surface could be monitored to compensate for the flutter. One means of monitoring the gap would be by using acoustic ranging. A pulse would be formed and reflected off from the rubber belt surface as a means of detecting distance; and thus location of the belt.

The data from the individual sensors is transmitted to a recording and analyzing means 36 to record the outputs from the sensors for further analysis. If the cords 14 in the belt 10 remain uniform along the length of the belt, then the signals from the sensors 32 would follow a regular pattern. However, a deviation in the pattern would indicate a change in permeability of one or more of the cords 14, which would generate a change in the field passing through the sensors 32 and that would generally be associated with some sort of damage and/or deterioration of the cords 14.

It is to be recognized that various modifications could be made In the present invention without departing from the basis teachings thereof.

What is claimed

1. An apparatus to detect faults in a plurality of magnetically permeable reinforcing cable members of a conveyor belt, where said belt comprises a main body portion having upper and lower surfaces, a longitudinal axis, a transverse axis, and a vertical axis, and said reinforcing members are longitudinally aligned and positioned within the main body portion at spaced intervals along the transverse axis of the belt, said apparatus comprising:
   a. a magnetic field coil means having an upper coil portion and a lower coil portion;
   b. a mounting means to mount and position said field coil means in an operating position so that the upper coil portion extends adjacent to, and transversely across, the upper surface of the belt, and the lower coil portion extends adjacent to, and transversely across, the lower surface of the belt,
   c. said coil means being arranged so that when the coil means is in the operating position, the upper coil portion produces an upper flux field extending at least partially through the cable members in the belt, and the lower coil portion produces a lower flux field extending at least partially through the cable members in the belt;
   d. a sensing means comprising a plurality of upper sensors, which are positioned at spaced intervals to extend transversely across, and adjacent to, the upper surface of the belt, and a plurality of lower sensors which are positioned at spaced intervals to extend transversely across, and adjacent to, the lower surface of the belt, each of said upper sensors being positioned and arranged to be located in the upper flux field to be responsive to absolute strength of the upper flux field at the location of that sensor, and each of said lower sensors being positioned and arranged to be located in the lower flux field to be responsive to the absolute field strength of the lower flux field at the location of that sensors, whereby, variations in the permeability of the magnetically permeable member are sensed by the sensors responding to variations in the absolute strength of the magnetic fields at the upper and lower sensors, with said variations indicating an anomaly in a portion of the magnetically permeable member positioned at the operating area, and flutter or oscillations of the belt in the operating area create contrasting differences in the magnetic field which are related to belt position and can be differentiated from magnetic field changes related to a belt condition that changes magnetic permeability.

2. The apparatus as recited in claim 1, wherein said coil means generates oscillating upper and lower magnetic fields.

3. The apparatus as recited in claim 1, wherein said sensors are Hall effect sensors.

4. A method to detect faults in a plurality of magnetically permeable reinforcing cable members of a conveyor belt, where said belt comprises a main body portion having upper and lower surfaces, a longitudinal axis, a transverse axis, and a vertical axis, and said reinforcing members are longitudinally aligned and positioned within the main body portion at spaced intervals along the transverse axis of the belt, said method comprising:

a. providing a magnetic field coil means having an upper coil portion and a lower coil portion;
   b. placing said field coil means in an operating position so that the upper coil portion extends adjacent to, and transversely across, the upper surface of the belt, and the lower coil portion extends adjacent to, and transversely across, the lower surface of the belt;
   c. causing the upper portion of the coil means to provide an upper flux field extending at least partially through the cable members in the belt, and the lower coil portion to provide a lower flux field extending at least partially through the cable members in the belt;
   d. providing a sensing means comprising a plurality of upper sensors, which are positioned at spaced intervals to extend transversely across, and adjacent to, the upper surface of the belt, and a plurality of lower sensors which are positioned at spaced intervals to extend transversely across, and adjacent to, the lower surface of the belt, each of said upper sensors being positioned and arranged to be located in the upper flux field to be responsive to absolute strength of the upper flux field at the location of that sensor, and each of said lower sensors being positioned and arranged to be located in the lower flux field to be responsive to the absolute field strength of the lower flux field at the location of that sensors,
   e. sensing variations in the permeability of the magnetically permeable member, with the sensors responding to variations in the absolute strength of the magnetic fields at the upper and lower sensors, with said variations indicating an anomaly in a portion of the magnetically permeable member positioned at the operating area, and sensing flutter or oscillations of the belt in the operating area which create contrasting differences in the magnetic field which are related to belt position and are differentiated from magnetic field changes related to a belt condition that changes magnetic permeability.

5. The method as recited in claim 4, wherein said upper and lower magnetic fields are oscillating magnetic fields.

6. The method as recited in claim 4, wherein said sensors are Hall effect sensors.

* * * * *